United States Patent [19]

Gergely et al.

[11] Patent Number: 5,138,153
[45] Date of Patent: Aug. 11, 1992

[54] DISTRIBUTED FIBER-OPTIC SENSOR WITH SUBSTANCE SELECTIVE PERMEABLE COATING

[75] Inventors: John S. Gergely; F. Monte Evens, both of Ponca City, Okla.

[73] Assignee: Conoco Inc., Ponca City, Okla.

[21] Appl. No.: 553,482

[22] Filed: Jul. 13, 1990

[51] Int. Cl.$^5$ .............................. H01J 5/16
[52] U.S. Cl. .................. 250/227.21; 250/227.18; 385/12
[58] Field of Search ........ 250/227.14, 227.18, 250/227.21, 227.23, 907, 904, 905, 231.1; 356/133, 70, 73.1; 340/605; 350/96.3, 96.31; 385/12, 123-128

[56] References Cited

U.S. PATENT DOCUMENTS

| | | | |
|---|---|---|---|
| 4,159,420 | 6/1979 | Tsunoda | 356/70 |
| 4,270,049 | 5/1981 | Tanaka et al. | 250/227 |
| 4,590,462 | 5/1986 | Moorehead | 340/605 |
| 4,634,856 | 1/1987 | Kirkham | 250/227 |
| 4,710,353 | 12/1987 | Tanaka et al. | 422/68 |
| 4,713,538 | 12/1987 | Theocharous | 250/227.23 |
| 4,735,212 | 4/1988 | Cohen | 250/227.18 |
| 4,763,009 | 8/1988 | Février et al. | 250/227.18 |
| 4,792,689 | 12/1988 | Peterson | 250/227.23 |
| 4,834,496 | 5/1989 | Blyler, Jr. et al. | 250/227.18 |
| 4,888,480 | 12/1989 | Dakin et al. | 250/227.23 |
| 4,894,532 | 1/1990 | Peterson et al. | 250/227.23 |

FOREIGN PATENT DOCUMENTS 0061884 10/1982 European Pat. Off. ........ 250/227.23

Primary Examiner—David C. Nelms
Assistant Examiner—Michael Messinger

[57] ABSTRACT

A sensor system comprises a fibe optic cable, or a fiber optic cable covered with a cladding, coated with a membrane that is sensitive to a particular substance to be detected. Contact with the material to be detected causes the membrane's index of refraction (normally less than that of the fiber core) to increase, decreasing the intensity of the light transmitted by the core. The fiber-optic sensor can be used to monitor one or more storage tanks for leakage by placing the fiber cable beneath the surface surrounding the tank(s).

23 Claims, 6 Drawing Sheets

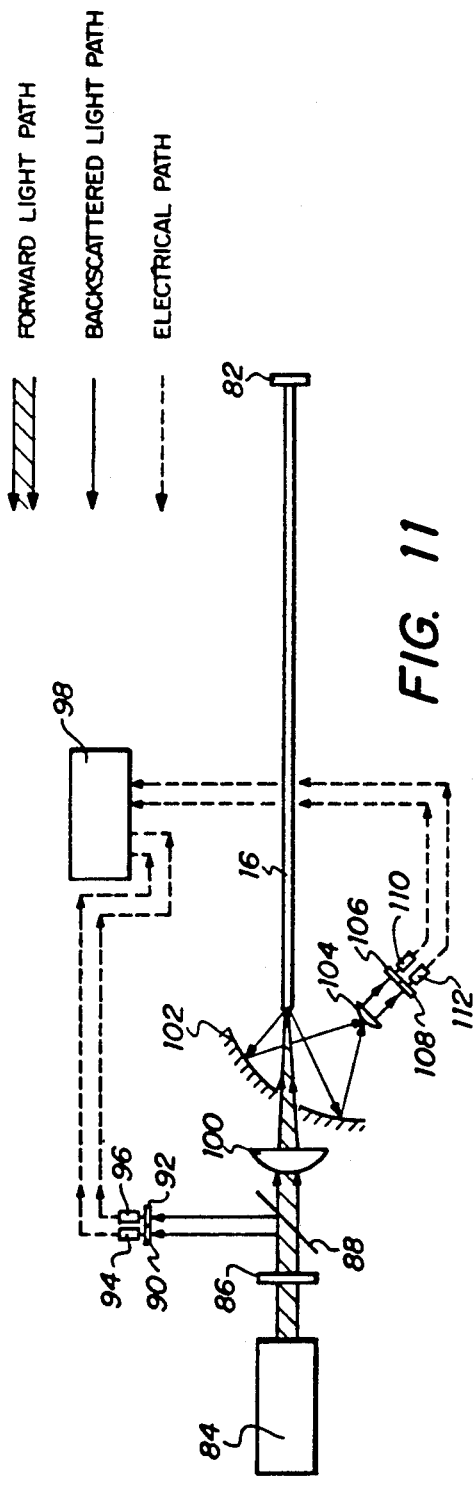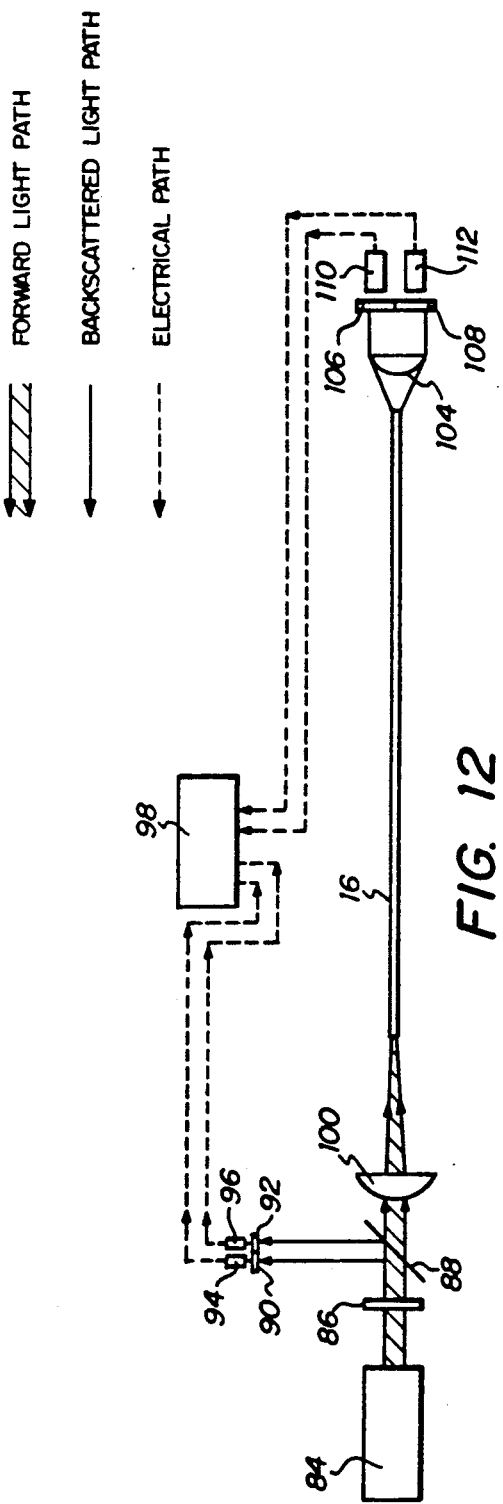

DISTRIBUTED FIBER-OPTIC SENSOR WITH SUBSTANCE SELECTIVE PERMEABLE COATING

BACKGROUND OF THE INVENTION

1. Field of the Invention

The present invention pertains to monitoring systems and more particularly to systems used to monitor many locations using only one sensor where the sensor is selective to monitor a single substance.

1. Related Prior Art

Present technology has illustrated several different methods for detecting unwanted leaks of environmentally destructive substances. The following patent is representative of a chemical/mechanical detection and warning system.

U.S. Pat. No. 4,590,462, titled "Oil Leakage Detection Apparatus", issued to Robert M. Moorhead relates to a chemically activated rotary actuator mechanism which reacts to exposure to hydrocarbons such as gasoline and oil. A detected leaks causes a rotor to forcibly rotate from a rest or static position. Spring members are used to load the rotor with, compressive forces which act through the rotational axis of the rotor to cause the mechanism to be unstable in the static position. The rotor is rotatably mounted in a body member and constrained from rotation with respect to the body member by means of shear pins which degrade when exposed to hydrocarbons. Rotation of the rotor shaft is utilized in generating an alarm.

Present technology has developed several different methods for using fiber optic cables. The following United States patents illustrate how the sensitivity and transmission qualities of fiber optic cables can be affected.

U.S. Pat. No. 4,270,049, titled "Liquid Leakage Detection System", issued to Masaya Tanaka et al. relates to a method for detecting a leakage of a liquid in terms of the drop in intensity of light rays traveling through a light guide core or optical fiber made of glass or synthetic resins. The change in intensity is due to the adhesion of the leaked liquid to the light guide.

U.S. Pat. No. 4,634,856, titled "Fiber Optic Moisture Sensor with Moisture-Absorbing Reflective Target", issued to Randy R. Kirkham relates to a method and apparatus for sensing moisture changes by utilizing optical fiber technology. One embodiment uses a reflective target at the end of an optical fiber. The reflectance of the target varies with its moisture content and can be detected by a remote unit at the opposite end of the fiber. A second embodiment utilizes changes in light loss along the fiber length. This can be attributed to changes in reflectance of cladding material as a function of its moisture content. It can also be affected by holes or inserts interposed in the cladding material and/or fiber. Changing light levels can also be coupled from one fiber to another in an assembly of fibers as a function of varying moisture content in their overlapping lengths of cladding material.

U.S. Pat. No. 4,710,353, titled "Corrosive Liquid Leak Detecting Sensor", issued to Satoshi Tanaka et al. relates to a detector for detecting leaks of a corrosive liquid such as strong acids or bases. This detector includes a light guide core having a covering which generates heat upon contact with the liquid to the detected, thereby changing the light transmissivity of the light guide which can be measured. The covering comprises a porous polymer having a salt within its pores such as an ammonium salt which dissolves in the liquid to be detected and generates heat.

SUMMARY OF THE INVENTION

A leakage monitoring system for above-ground and below-ground storage tanks utilizes fiber optic technology. The monitoring system has a sensor which consists of an optical fiber coated with a special membrane that is selectively reactive with a specific substance. These fibers can be run for extended lengths in, around and under storage tanks in such as a tank farm. A centrally located optical generation and detection station provides source light through the optical fiber along with a detector for detecting changes in a light field within the optical network, which changes are susceptible of scaler evaluation, and a read out to provide leakage notice, alarm, etc. The present invention discloses two separate embodiments, first, a differential absorption system and second, a long path absorption system.

BRIEF DESCRIPTION OF THE DRAWINGS

FIG. 11 illustrates the apparatus for the long path absorption scheme with a reflector at the end of the fiber.

FIG. 12 illustrates the apparatus for the long path absorption scheme without a reflector at the end of the fiber.

DESCRIPTION OF THE PREFERRED EMBODIMENT

The present invention permits the monitoring of many locations using only one sensor. The present invention also eliminates the need for several sensors and numerous data lines. The sensor is selective to monitor only a predetermined substance.

Prior art has not disclosed sensors for the selective monitoring of substances using a distributed fiber. Others have monitored pressure and temperature using distributed fibers.

The Environmental Protection Agency may require monitoring of above ground storage tanks, which includes tank farms that can have hundreds of tanks. Therefore, there is a great need to have a simple, reliable, and cost-effective monitoring system. The present invention is such a system, which uses a single fiber-optic cable to monitor one or more tanks. This eliminates the need for multiple detectors and many data lines.

The present invention is a new type of fiber-optic sensing system that can selectively detect and locate substances at various locations along the entire length of a fiber cable. A fiber is coated with a special membrane that absorbs or passes only the substance to be monitored, depending on which of two types of sensors are used.

Figure 1:
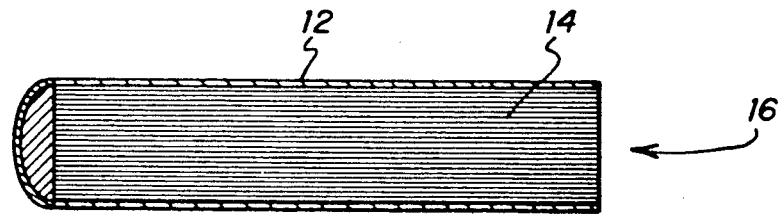
FIG. 1 is an illustration of an optical fiber where a membrane is attached directly to the core of the fiber.

In FIG. 1, a membrane 12 is attached directly to the core 14 of a fiber 16. In this configuration, membrane 12 must have an index of refraction less than that of core 14 for light to propagate in core 14 by total internal reflection. To monitor the sample, membrane 12 selectively absorbs the sample which increases its index of refraction. This increase causes more light traveling in core 14 to couple into the evanescent field in membrane 12.

Figure 2:
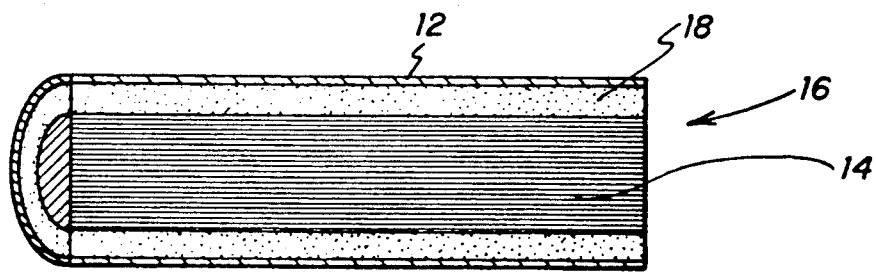
FIG. 2 is an illustration of an optical fiber where a membrane is placed around a cladding of the fiber.

In FIG. 2, membrane 12 is placed around cladding 18 of fiber 16. In this case, membrane 12 selectively passes the sample to be monitored which in turn is absorbed by cladding 18. The absorbed sample makes cladding 18 "swell" and increases its index of refraction causing more light in a core 14 to be coupled into the evanescent field in cladding 18.

In both cases, the increase coupling to the evanescent field causes a decrease in power in core 14 of fiber 16. This decrease is detected at either the input or output end of the fiber depending on what monitoring scheme is used.

Figure 3:
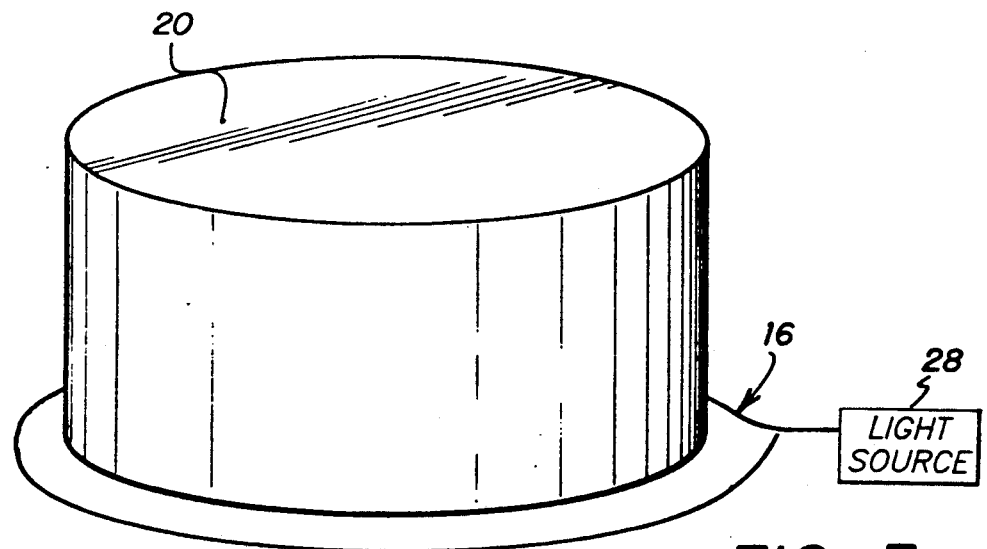
FIG. 3 illustrates the deployment of a fiber optic monitoring system for an above-ground tank.

The system of the present invention can monitor above-ground and below-ground storage tanks. The deployment of the system for above-ground tanks is shown in FIG. 3. Fiber 16 is placed a nominal distance below the ground surface and completely encircles tank 20 If the tank leaks, the leaking substance comes in contact with fiber 16 and passes through selective membrane 12, which changes the index of refraction surrounding fiber 16. This change then affects either a continuous light beam or pulses traveling down the fiber. The former will give an average concentration of the leaking substance along fiber 16, indicating that tank 20 is leaking, but will not determine the leak location. The latter will give spatially resolved measurements which will locate where tank 20 is leaking.

Figure 4:
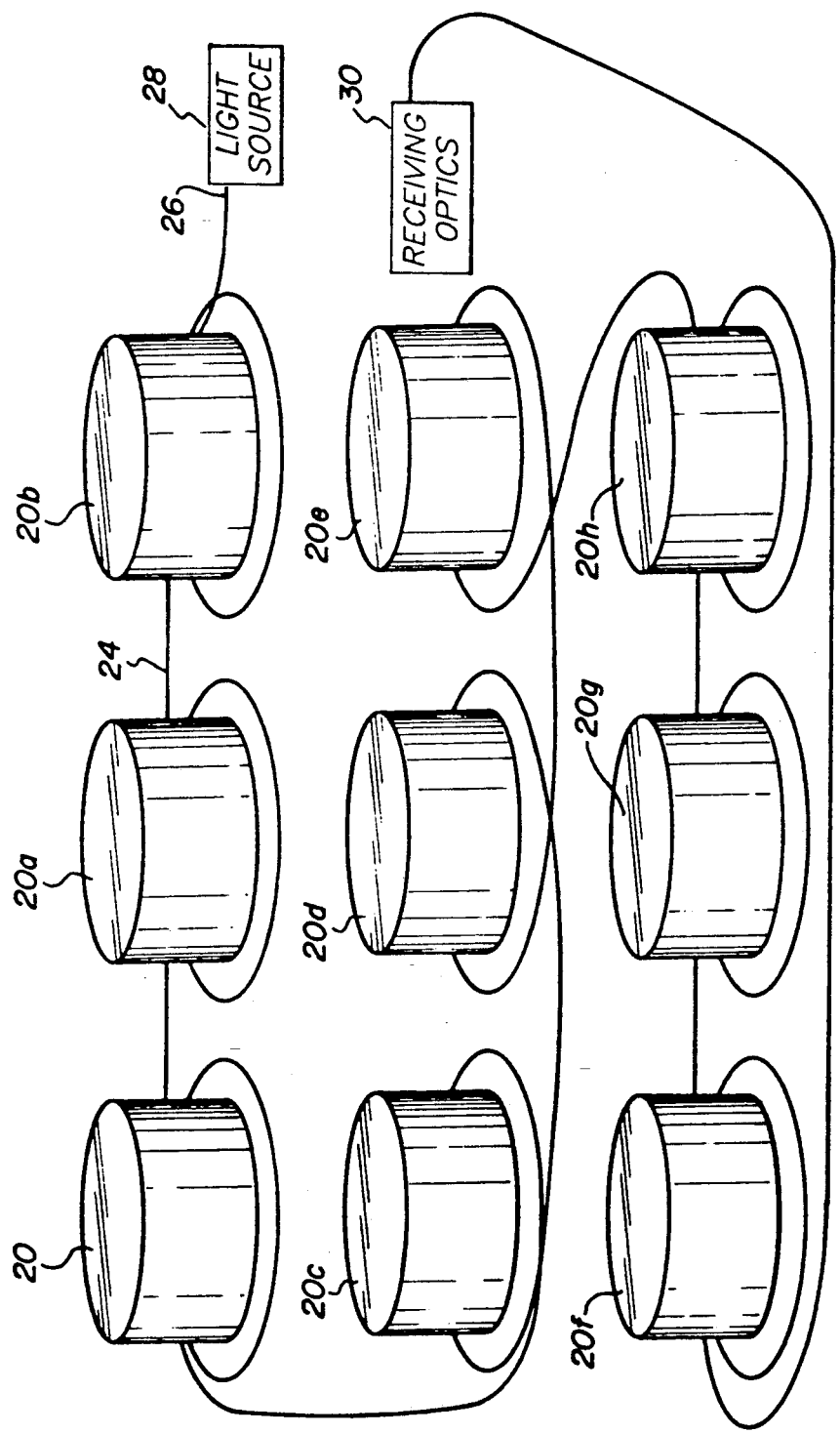
FIG. 4 illustrates a fiber optic monitoring system to monitor an entire tank farm using a differential absorption method.
Figure 5:
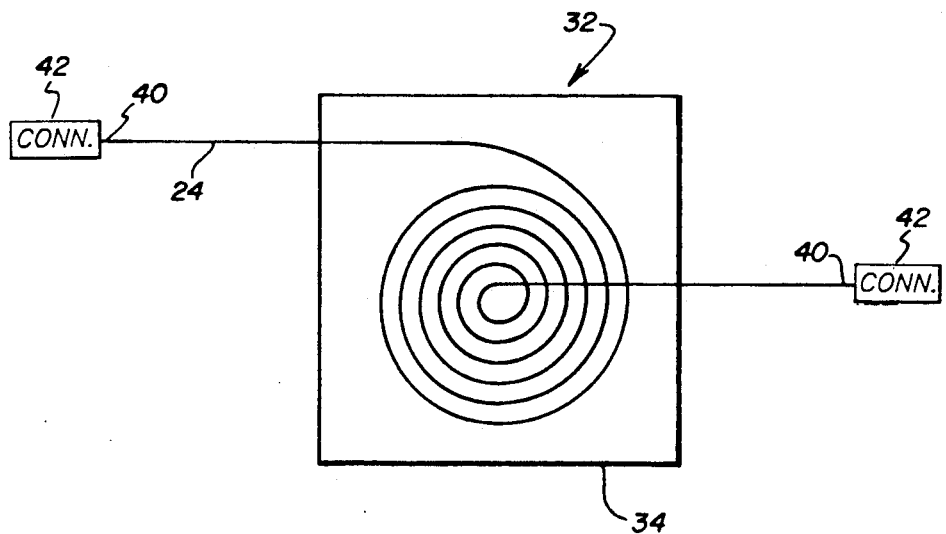
FIG. 5 illustrates a fiber optic selective sensor made by spinning the fiber into individual coiled sensors.
Figure 6:
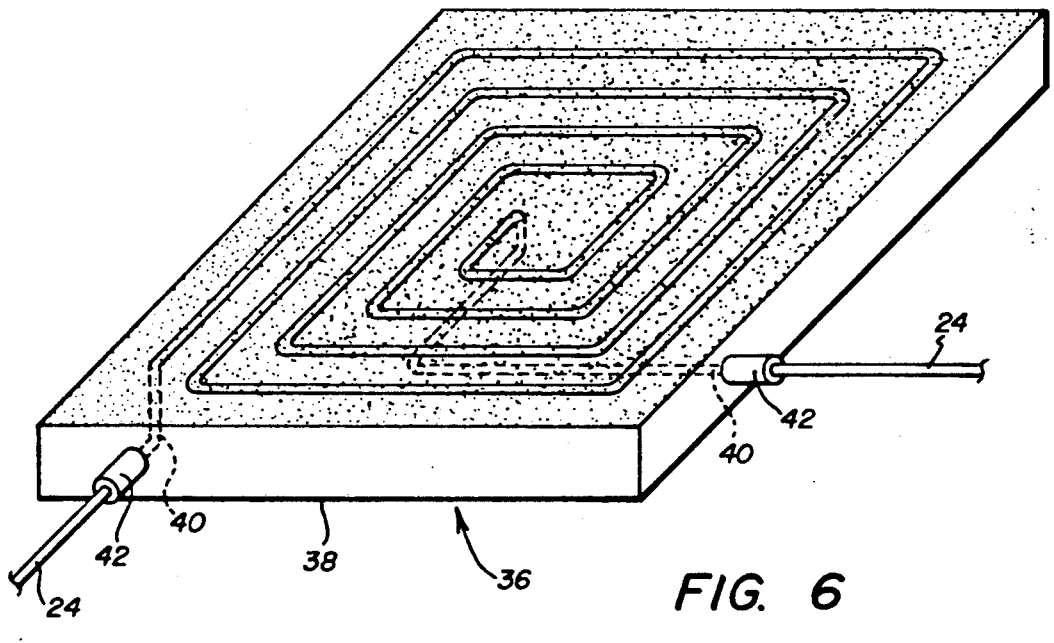
FIG. 6 illustrates a fiber optic selective sensor made by fabricating planar wave guide sensors.

To monitor an entire tank farm, the differential absorption method using pulses is used, as shown in FIG. 4. The entire tank farm, consisting of multiple tanks 20a-20h, can be monitored using only one long fiber cable 24 without the need of many detectors and numerous data lines. The input end 26 of fiber cable 24, connected to a light source 28 and receiving optics 30, both of which are located in a control room. Fiber cable 24 is placed around each tank 20a-20h in series. The light pulses are launched into fiber 24, and knowing the speed of light through fiber 24, the location and the relative concentration of the substance can be found. To increase the sensitivity of the system, the length of fiber 24 is increased in a given area. This is done by spinning hundreds of meters of fiber 24 into individual coiled sensors 32 in an encasement 34, as illustrated in FIG. 5 or fabricating planar wave guide sensors 36 in a substrate 38, as shown in FIG. 6. In each case, ends 40 of fiber 24 are provided with connectors 42 for coupling into substrate 38. The planar wave guide sensor is made using integrated circuit fabrication methods. The wave guide sensors will avoid false signals found in coiled sensors caused by pressure changes as the cladding "swells."

Similar deployments can be made for underground storage tanks as well.

Figure 7:
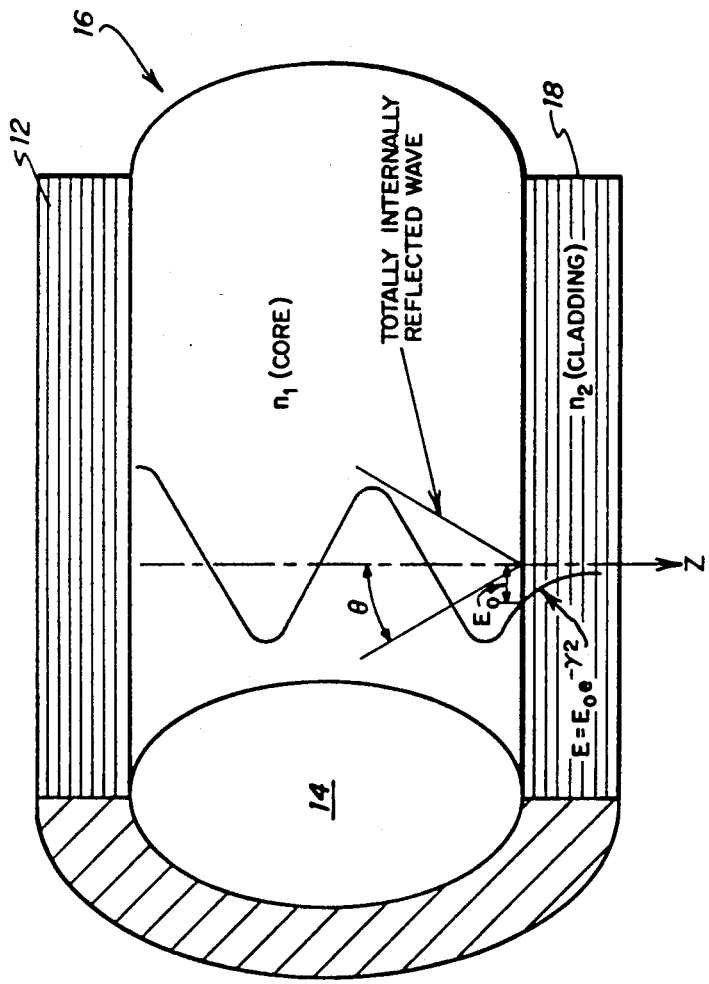
FIG. 7 illustrates internal light reflectivity of the fiber core, and evanescent wave decay within the cladding.

An important mechanism on which the fiber sensor of the present invention relies is that the absorbed sample changes the refractive index of the medium surrounding core 14 of fiber 16. When this happens, more of the light inside core 14 escapes through the evanescent field which exists outside core 14. The evanescent wave outside core 14 is given by:

$$E = E_o e^{-\gamma z} \quad (1)$$

where z is the normal direction of the surface of fiber core 14, as shown in FIG. 7, $$\gamma = \left(\frac{2\pi}{\lambda_1}\right)(\sin^2 \theta - n_{21}^2)^{\frac{1}{2}} \quad (2)$$

where:
$\theta$ = angle of incidence $$n_{21} = \frac{n_2}{n_1} \quad (3)$$

where:
$n_2$ = the refractive index of the medium surrounding the fiber core.
$n_1$ = the refractive index of the fiber core.
$\lambda_1$ = the wavelength of light in the core.

The transmitted intensity through the fiber with losses to the evanescent field is given by:

$$I = I_o 10^{-a_o[C]L} \quad (4)$$

where:

$$a_o = \eta_p a_c \quad (5)$$

I = transmitted intensity.
$I_o$ = intensity with no sample absorbed.
[C] = concentration of sample in moles/liter.
$a_o$ = Beer's law molar absorptivity of the sample.

$$\eta_p = \frac{P_m}{P_t}$$

where:
$P_n$ is the evanescent field intensity and $P_t$ is the light intensity in the fiber core.

$\eta_p$ is also equal to $\frac{k}{v}$, where:

$$v = (2\pi r_f/\lambda_1)(n_1^2 - n_2^2)^{\frac{1}{2}}$$

and $r_f$ = radius of the core.
So, $$I = I_o 10^{-a_o \eta_p [C]L} \quad (7)$$

Equation 7 can be written as $$I = I_o e^{-\sigma n L} \quad (8)$$

where:

$n = N[C] \times 10^3$ in number of molecules per cm$^3$ $$N = 6.023 \times 10^{23} \frac{\text{molecules}}{\text{mole}} \text{ (Avogadro's number)}.$$

So, $$\sigma = \frac{2303 \, \alpha_c \, \eta_p}{N} = 3.81 \times 10^{-19} \, \alpha_c \, \eta_p \text{ (cm}^2) \quad (9)$$

The backscattered or forward scattered signal from a medium at range R is given by:

$$P_A(R) = \frac{\rho}{\pi} K P_o \frac{A}{R^2} \exp - 2 \int_o^R \alpha_A(r) dr \quad (10)$$

where:

$P_A(R)$ = received power from range R.
$P_o$ = transmitted power.
$K$ = optical system efficiency.
$A$ = area of receiving optics.
$(\rho/\pi)$ = effective reflectivity of the medium.
$\alpha_A(r)$ = volume extinction coefficient of the fiber at range r.
where:

$$\alpha_A(r) = \sigma n(r) + \alpha_{SC}(r) \quad (11)$$

$\alpha_{SC}(r)$ = scattering coefficient of the fiber.

Figure 8:
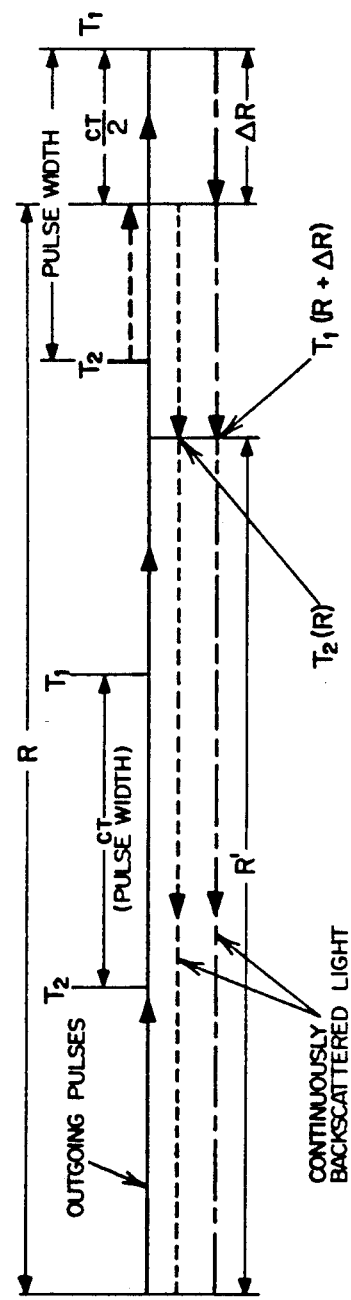
FIG. 8 illustrates the spatial resolution for a pulse traveling down an optical fiber.

The portion of the returned signal due to Raman, Mie, and Rayleigh backscatter is taken into account in the effective reflectivity term $\rho/\pi$. The depth resolution, is shown in FIG. 8, and is given by $\Delta R = c\tau/2$, where $\tau = \tau_P + \tau_D$, is the sum of the laser pulse width $\tau_P$ and the detector integration time $\tau_D$. If a fluorescence scheme is used, then $\tau_F$, the fluorescence lifetime of the sample, is added to the total $\tau$.

In FIG. 8, the front of a pulse (T$_1$) is illustrated as backscattering to point R'. The back of the pulse (T$_2$) travels to point R then backscatters to point R'. They both arrive at point R' at the same time giving a spatial resolution of $\Delta R$.

Figure 9:
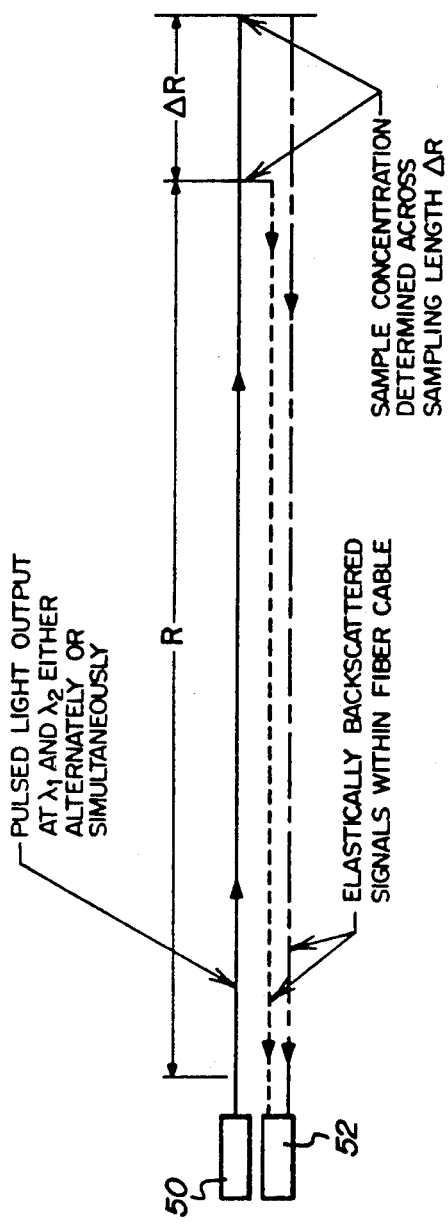
FIG. 9 illustrates a differential absorption method.

The system of the present invention uses both the differential absorption or long path absorption techniques. The differential absorption scheme determines the concentration of a sample at an arbitrary point, the distance R in the fiber, by measuring the optical resonance absorption due to the sample across an incremental path length, $\Delta R$. This is illustrated schematically in FIG. 9. The absorption across $\Delta R$ is obtained from the relative attenuation of two laser beams at close-lying wavelengths, $\lambda_1$ and $\lambda_2$, respectively, on and off the resonance absorption of the sample molecule in question. The laser beams are generated by a light source 50 and detected by detectors 52. The relative attenuation is determined from comparisons (at the receiver) of the Rayleigh and Mie elastic backscatter from the two laser beams as they traverse $\Delta R$ in the fiber. Appropriate temporal resolution at the receiver permits determination of both R and $\Delta R$, the range, and spatial resolution of the sample distribution, as shown in FIG. 8.

Several features of this scheme should be noted. First, since the receiver signal is simply the elastic backscattered component of the transmitted signal, this permits the use of very narrow bandwidth receivers (if possible, down to the bandwidth of the transmitted signal). This is an important factor in reducing undesirable background noise.

Second, the received signal that is due to the elastic scattering from fiber 16 is relatively large and thus easily detected.

Third, since this scheme determines the sample concentration by an absorption method, the achievable detection sensitivity is high even where the required spatial resolution is high (or equivalently, where the sampling lengths are small).

For differential absorption, the effective reflectivity in an unconfined volume is given by:

$$\frac{\rho}{\pi} = \frac{c\tau_p}{2} [\beta_R(r, \lambda) + \beta_M(r, \lambda)] \quad (12)$$

where:

c = speed of light through the volume
$\tau_P$ = laser pulse width ($\tau_D < < \tau_P$)
$\beta_R (r,\lambda)$ = Rayleigh backscatter coefficient.
$\beta_M (r,\lambda)$ = Mie backscatter coefficient.

For light traveling through a fiber cable, the R$^2$ dependence in Equation 10 is essentially cancelled, because the backscattered light is confined in the fiber by total internal reflection and does not radiate in an R$^2$ fashion.

The effective reflectivity becomes $$\frac{\rho}{\pi} = \frac{R^2}{A} \frac{c\tau_p}{2} [\beta_R(R, \lambda) + \beta_M(R, \lambda)] \quad (13)$$

Substituting this effective reflectivity into Equation 10 gives:

$$P_A(R, \lambda) = \frac{c\tau_p}{2} [\beta_R(R, \lambda) +$$

$$\beta_M(R, \lambda)] K P_o(\lambda) \exp - 2 \int_o^R [\alpha_{SC}(r, \lambda) + \sigma_{ABS}(r, \lambda) n_r] dr \quad (14)$$

where:

$\alpha_{SC}(r,\lambda) = \alpha_R(r,\lambda) + \alpha_M(r,\lambda)$, the volume scattering coefficient of the fiber without absorption.

$\alpha_R(r,\lambda)$ = the Rayleigh volume scattering coefficient of the fiber.

$\alpha_M(r,\lambda)$ = the Mie volume scattering coefficient of the fiber.

The other parameters were previously defined.

An expression for $\bar{n}_r$ averaged over a distance $\Delta R$ can be obtained from Equation 14 for $P(R,\lambda)$ by forming the difference of the logarithm of P (R) evaluated at R and R + $\Delta R$ for both a frequency on the absorption peak ($\lambda_1$) and to the absorption trough ($\lambda_2$). These equations are shown below:

$$\ln P_A(r, \lambda_1) - \ln P_A(R + \Delta R, \lambda_1) = \frac{-2\Delta R}{R} + \quad (15)$$

$$\ln[\beta_R(R, \lambda_1) + \beta_M(R, \lambda_1)] - \ln[\beta_R(R + \Delta R, \lambda_1) +$$

$$\beta_M(R + \Delta R, \lambda_1)] + 2\alpha_{SC}(\lambda_1)\Delta R + 2\sigma_{ABS}(\lambda_1)n_r\Delta R.$$

$$\ln P_A(R, \lambda_2) - \ln P_A(R + \Delta R, \lambda_2) = \frac{-2\Delta R}{R} + \quad (16)$$

$$\ln[\beta_R(R, \lambda_2) + \beta_M(R, \lambda_2)] - \ln[\beta_R(R + \Delta R, \lambda_2) +$$

$$\beta_M(R + \Delta R, \lambda_2)] + 2\alpha_{SC}(\lambda_2)\Delta R + 2\sigma_{ABS}(\lambda_2)n_r\Delta R.$$

An expression for $\bar{n}_r$, the value of $n_r$ averaged for the depth resolution $\Delta R$ at range R, can be obtained from Equations 15 and 16 as:

$$n_r = \frac{1}{2\Delta\sigma\Delta R}\left[\ln\frac{P_r(R, \lambda_1)}{P_r(R + \Delta R, \lambda_1)} - \ln\frac{P_r(R, \lambda_2)}{P_r(R + \Delta R, \lambda_2)} + S + S'\right] \quad (17)$$

where, $$S = -2[\alpha_{SC}(\lambda_1) - \alpha_{SC}(\lambda_2)]\Delta R. \quad (18)$$

$\alpha_{SC}(\lambda) = \alpha_R(\lambda) + \alpha_M(\lambda)$, the total volume scattering coefficient of the fiber neglecting absorption, averaged over $\Delta R$, and $\Delta\sigma = \sigma_{ABS}(\lambda_1) - \sigma_{ABS}(\lambda_2)$, the difference in absorption cross sections.

$$S' = \ln\left[\frac{\beta_R(R + \Delta R, \lambda_1) + \beta_M(R + \Delta R, \lambda_1)}{\beta_R(R, \lambda_1) + \beta_M(R, \lambda_1)}\right] - \ln\left[\frac{\beta_R(R + \Delta R, \lambda_2) + \beta_M(R + \Delta R, \lambda_2)}{\beta_R(R, \lambda_2) + \beta_M(R, \lambda_2)}\right] \quad (19)$$

In order to evaluate Equation 17, it is necessary to know the magnitudes of S and S'. These quantities are, in general, unknown. However, if these coefficients do not change significantly over the spectral intervals $\lambda_1 - \lambda_2$, then S and S' can be taken to be zero. Therefore, making these assumptions, Equation 17 reduces to:

$$n_r = \frac{1}{2\Delta\sigma\Delta R}\left[\ln\frac{\frac{P_r(R, \lambda_1)}{P_r(R, \lambda_2)}}{\frac{P_r(R + \Delta R, \lambda_1)}{P_r(R + \Delta R, \lambda_2)}}\right] \quad (20)$$

or, $$n_r = \frac{\ln(1 + \Delta F_r)}{2\Delta\sigma\Delta R} \quad (21)$$

where:

$\Delta F_r$ = the fractional change in the ratio of ratios of the received signals.

As can be seen from Equation 21, the sensitivity of sample detection is improved by, first, the ability of the instrumentation to detect smaller changes in $\Delta F_r$, second, increasing the sampling length, $\Delta R$ (at a cost of decreasing spatial resolution), and, third, a large resonance absorption cross section, $\sigma_{\lambda 1}$, and a small off resonance cross section, $\sigma_{\lambda 2}$.

In the technique for long path absorption, the average sample concentration along the entire fiber 16 is determined from measurements of the relative attenuation along the length of the probed path, R, of two laser beams at close-lying wavelengths, $\lambda_1$ and $\lambda_2$, respectively, on and off a resonance absorption peak of the sample in questions. This scheme has the disadvantages of needing a remote detector or reflective target to receive or reflect the transmitted beam at the end of the fiber, and lacks depth resolved measurements. The advantages of this scheme are its good sensitivity and the use of low power light sources.

The received power at the detector is given by Equation 10 with the appropriate effective reflectivity terms inserted Again, since the light is traveling in a fiber, the range-squared dependence is effectively cancelled.

When using a retroreflector at the end of the fiber, the effective reflectivity term is:

$$\frac{\rho}{\pi} = \frac{R^2\psi}{A} \quad (22)$$

where $\Psi$ is the optical efficiency of the retroreflector at the end of the fiber.

Inserting Equation 22 into Equation 10, an expression for the average sample concentration over R can be obtained by taking the difference between the logarithms of the received powers at range zero and R from the off-line and on-line wavelengths, respectively:

$$\ln P_r(R, \lambda_2) - \ln P_r(R, \lambda_1) = \ln P_o(\lambda_2) - \ln P_o(\lambda_1) + \quad (23)$$
$$2[\alpha_{SC}(\lambda_1) - \alpha_{SC}(\lambda_2)]R + 2[\alpha_{ABS}(\lambda_1) - \sigma_{ABS}(\lambda_2)]n_r R,$$

where:

$\alpha_{SC}(\lambda) = \alpha_R(\lambda) + \alpha_M(\lambda)$, the total volume scattering coefficient of the fiber without absorption averaged over R, and $\bar{n}_r$ = the average sample concentration over R.

Solving for the average sample concentration yields:

$$n_r = \frac{1}{2\Delta\sigma R}\left[\ln\frac{P_o(\lambda_1)}{P_o(\lambda_2)} - \ln\frac{P_r(R, \lambda_1)}{P_r(R, \lambda_2)} + S''\right] \quad (24)$$

where:

$S'' = -2[\alpha_{SC}(\lambda_1) - \alpha_{SC}(\lambda_2)]R$, and $\Delta\sigma = \sigma_{ABS}(\lambda_1) - \sigma_{ABS}(\lambda_2)$, the difference in absorption cross sections.

In order to evaluate Equation 24 exactly, it is necessary to know the magnitude of the S'' term. This quantity is, in general, unknown. However, if the $\alpha$ coefficients do not change significantly over the spectral interval, $\lambda_1 - \lambda_2$ (which is true for the case for close-lying wavelengths), then S'' can be taken to be zero. Therefore, Equation 24 reduces to:

$$n_r = \frac{1}{2\Delta\sigma R}\ln\left[\frac{\frac{P_o(\lambda_1)}{P_o(\lambda_2)}}{\frac{P_r(R, \lambda_1)}{P_r(R, \lambda_2)}}\right] \quad (25)$$

or, $$n_r = \frac{\ln(1 + \Delta F_r)}{2\Delta\sigma R} \quad (26)$$

where:

$\Delta F_r$ = the fractional change in the ratio of ratios of the on-line and off-line transmitted and received powers respectively.

Figure 10:
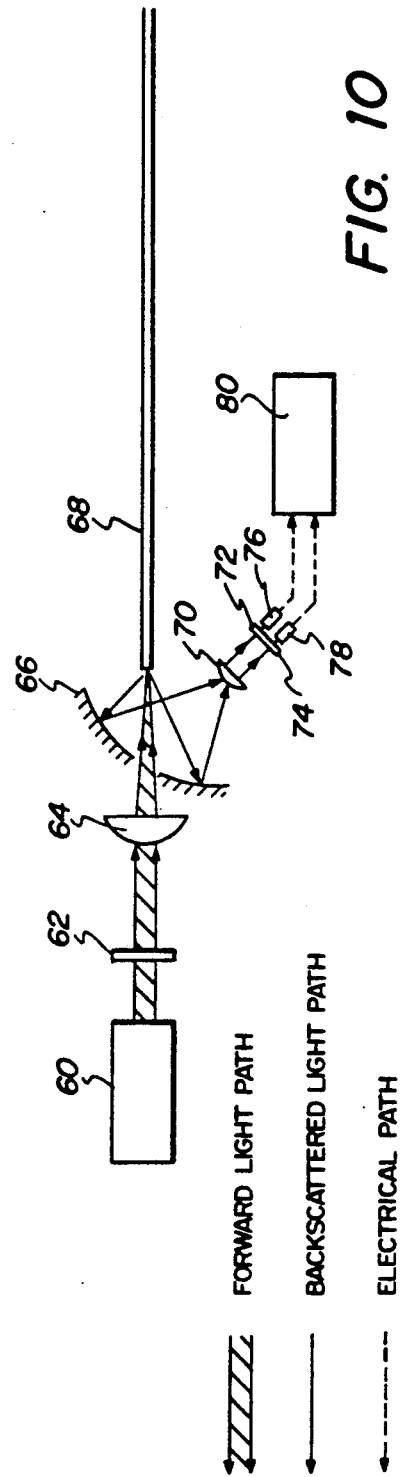
FIG. 10 illustrates an apparatus for the differential absorption scheme of FIG. 9.

FIG. 10 shows the equipment layout for the differential absorption scheme. To monitor a tank farm, which may contain hundreds of tanks, requires a modest amount of equipment. Light from a pulsed light source 60 (e.g., a two-wavelength dye laser emitting alternate or simultaneous pulses, tunable diode laser, or a wide-band arc lamp) passes through a filter 62 that passes two close-lying wavelengths, $\lambda_1$ and $\lambda_2$. The filter is not required if a dual wavelength laser, a tunable laser, or a combination of two sources are used. Lens 64 directs the light through directional coupler 66 and couples the light into fiber cable 68. The light pulse travels down the fiber and backscatters continuously. The backscattered two-wavelength signals exit fiber cable 68 at the point where the light originally entered. The backscattered signals are directed to collimating lens 70 by directional coupler 66. Filters 72 and 74 each pass only one of the two backscattered wavelengths. Filter 72 passes $\lambda_1$ and filter 74 passes $\lambda_2$. Behind filter 72 is detector 76 that detects $\lambda_1$, and behind filter 74 is detector 78 that detects $\lambda_2$. The signals from detectors 76 and 78 are displayed and stored on a data acquisition system 80 such as the Data 6000 with a 640 plug-in from Data Precision, Inc. Sample concentrations are calculated from the time-resolved signals off the Data 6000 using Equation 21. Range calculations or position of the leaks are determined from time-of-flight measurements of the pulse traveling down the fiber.

A commercially available, two-channel, optical time domain reflectometer (OTDR) may be used in place of the lens 70, filters 72 and 74, detectors 76 and 78, and data acquisition system 80. The only modifications to the ODTR would be to replace the standard filters with filters that pass $\lambda_1$ and $\lambda_2$.

FIGS. 11 and 12 illustrate the apparatus for the long path absorption scheme. The system in FIG. 11 uses a retroreflector or reflective coating 82 at the end of the fiber, and the system in FIG. 12 has receiving optics and detectors at the far end of the fiber. Both schemes can use either a pulsed or a continuous wave (cw) light source, because only the average sample concentration is determined along the entire length of the fiber cable. The scheme shown in FIG. 11 works in the following way. Light from a pulsed or cw source 84 is filtered by two-wavelength filter 86 which passes $\lambda_1$ and $\lambda_2$. These wavelengths strike beam splitter 88 which taps off about eight percent of the light. Fifty percent of this light strikes filter 90 which passes $\lambda_1$, and the remaining 50 percent strikes filter 92 which passes $\lambda_2$. Detector 94 behind filter 90 detects the power of $\lambda_1$, and detector 96 behind filter 92 detects the power of $\lambda_2$. These reference signals, now electrical, are sent to a processor 98, such as a Data 6000 or an IBM PC to be used in calculating the concentrations of the sample along the fiber. Before this can be done, the power readings of $\lambda_1$ and $\lambda_2$, after traveling through the fiber, are needed.

To obtain these readings, lens 100 couples $\lambda_1$ and $\lambda_2$, into fiber cable 16 through directional coupler 102. The light hits retroreflector 82, returns through fiber 16, is directed to collimating lens 104 by directional coupler 102. The collimated light then strikes the same type of dual filter 106, 108 and dual detector 110, 112 arrangement used to detect the reference signals, similar to filters 90 and 92 and detectors 94 and 96. The signals from detectors 110 and 112 are fed into processor 98. Using the signals from detectors 94, 96, 110, 112 and Equation 26, the average sample concentration along the entire fiber is calculated.

For the system shown in FIG. 12, it is possible to use the same light source 84, filter 86, beam splitter 88, dual filters 90 and 92, dual detectors 94 and 96, processor 98, coupling lens 100, and fiber 16 as the system shown in FIG. 11. However, in this case lens 104, filters 106, 108 and detectors 110, 112 are located at the far end of fiber 16. The readings from all four detectors, combined with Equation 26 (without the 2 in the denominator) yields the average sample concentration along the entire length of the fiber 16 as calculated in processor 98. The "2" is deleted from the denominator in Equation 26 because the light is attenuated by a single pass through the fiber as compared with two passes with the other schemes.

Fluorescence and Raman detection techniques can also be used if the samples fluoresce or have Raman bands. The system is not limited to the detection of liquids, but can also be used to monitor for gases as well.

Furthermore, if a cw or pulsed wide-band or tunable source is used with a spectrometer or diode array as the detection system in the Long Path Absorption scheme, a spectrum of the sample averaged over the entire length of the fiber sensor can be obtained.

In addition, if a pulsed tunable or pulsed wide-band source is used with a fast diode array or spectrometer/streak camera system, then spectra of the sample can be obtained at discrete locations along the entire length of the fiber sensor.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

We claim:

1. A monitoring system comprising:
   a light generation means for producing a beam of light;
   a distributed fiber sensor connected to said light for transmitting said beam of light, said distributed fiber sensor having a fiber optic cable with a substance selective permeable coating said coating only permitting permeation of substances having an index of refraction greater than said fiber optic cable; and
   light detection means connected to said distributed fiber sensor;
   sensor associated with said light detection means for receiving said transmitted beam of light and determining the intensity of said transmitted beam of light.

2. The monitoring system according got claim 1 wherein said distributed fiber sensor includes a differential absorption fiber optic cable.

3. The monitoring system according to claim 2 wherein said light generation means includes means for generating light pulses.

4. The monitoring system according to claim 1 wherein said distributed fiber sensor includes a long path absorption fiber optic cable means.

5. The monitoring system according to claim 4 wherein said fiber optic cable includes a retroreflector at one end to reflect said beam of light back toward said light generation means and said light detection means is connected to the same end of said distributed fiber sensor as said light generation means.

6. The monitoring system according to claim 5 wherein said fiber optic cable means includes a retroreflector at one end to reflect said beam of light back toward said light generation means and said light detection means is connected to the same end of said distributed fiber sensor as said light generation means.

7. The monitoring system according to claim 5 wherein said light generation means includes means for generating a continuous light beam.

8. The monitoring system according to claim 1 wherein said fiber optic cable with a substance selective permeable coating includes a fiber optic cable with a membrane around the fiber core.

9. The monitoring system according to claim 1 wherein said fiber optic cable with a substance selective permeable coating includes a fiber core covered with a cladding which is coated with a substance selective membrane.

10. A system for monitoring substance leakage having a light source and a light detector to detect light intensity, said system comprising:
   a fiber optic cable means connected between said light source and said detector for transmitting light therebetween; and
   substance selective means coating said fiber optic cable means for passing preselected substances to affect light transmission through said fiber optic cable means by increasing the index of refraction of said fiber optic cable means.

11. The system for monitoring according to claim 10 wherein said light source includes means for generating light pulses.

12. The system for monitoring according to claim 10 wherein said light source includes means for generating light having two distinct wavelengths, each on alternate pulses.

13. The system for monitoring according to claim 12 wherein said fiber optic cable means includes a differential absorption fiber optic cable.

14. The system for monitoring according to claim 10 wherein said light source includes means for generating light having two distinct wavelengths, each on simultaneously emitted pulses.

15. The system for monitoring according to claim 11 wherein said fiber optic cable means includes a long path absorption fiber optic cable.

16. The system for monitoring according to claim 15 wherein the fiber optic cable includes a retroreflector at one end to reflect said beam of light back toward said light source and said light detector is located at the same end as said light source.

17. The system for monitoring according to claim 15 wherein said light source includes means for generating light pulses.

18. The system for monitoring according to claim 15 wherein said light source includes means for generating a continuous light beam.

19. The system for monitoring according to claim 10 wherein said fiber optic cable with a substance selective permeable coating includes a fiber optic cable with a membrane around the fiber core.

20. The system for monitoring according to claim 10 wherein said fiber optic cable with a substance selective permeable coating includes a fiber core covered with a cladding which is coated with a substance selective membrane.

21. A method for determining substance leaks in a system having a light source, a fiber optic cable and a light intensity detector comprising the steps of:
   passing light through said fiber optic cable from said light source to said light intensity detector;
   covering said fiber optic cable with a coating that is selective permeable to said substance;
   passing said substance through said coating, and
   increasing the index of refraction for said fiber optic cable whenever said substance passes through said coating.

22. The method according to claim 21 wherein said covering said fiber optic cable includes placing a membrane around the core of said fiber optic cable.

23. The method according to claim 21 wherein said covering said fiber optic cable includes placing a cladding which is coated with a substance selective membrane around the core of said fiber optic cable.

* * * * *

UNITED STATES PATENT AND TRADEMARK OFFICE
CERTIFICATE OF CORRECTION

PATENT NO. : 5,138,153
DATED : August 11, 1992
INVENTOR(S) : John S. Gergely et al.

Page 1 of 3

It is certified that error appears in the above-indentified patent and that said Letters Patent is hereby corrected as shown below:

Column 4, line 34, in the equation, replace "$\alpha_o$" with --$\alpha_e$--.

Column 4, line 38, in the equation, replace "$\alpha_o$" with --$\alpha_e$--.

Column 4, line 43, "$\alpha_o$" should be --$\alpha_c$--.

Column 4, line 50, "$P_n$" should be --$P_m$--.

Column 4, line 63, in the equation, "$\alpha_o$" should be --$\alpha_c$--.

Column 6, line 62, in the equation, replace "$n_r$" with --$\bar{n}_r$--.

Column 6, line 67, in the equation, replace "$n_r$" with --$\bar{n}_r$--.

Column 7, line 6, in the equation, replace "$n_r$" with --$\bar{n}_r$--.

Column 7, line 15, in the equation (both occurrences), replace "$\alpha_{sc}$" with --$\bar{\alpha}_{sc}$--.

Column 7, line 16, replace "$\alpha_{SC}$" with --$\alpha_{sc}$--.

Column 7, line 16, replace "$\alpha_R$" with --$\bar{\alpha}_r$--.

Column 7, line 16, replace "$\alpha_M$" with --$\bar{\alpha}_m$--.

UNITED STATES PATENT AND TRADEMARK OFFICE
CERTIFICATE OF CORRECTION

PATENT NO. : 5,138,153
DATED : August 11, 1992
INVENTOR(S) : John S. Gergely et al.

Page 2 of 3

It is certified that error appears in the above-indentified patent and that said Letters Patent is hereby corrected as shown below:

Column 7, line 41, in the equation, "$n_r$" with --$\bar{n}_r$--.

Column 7, line 46, in the equation, "$n_r$" with --$\bar{n}_r$--.

Column 8, line 23, in the equation, replace "$\alpha_{SC}$" (both occurrences) with --$\bar{\alpha}_{sc}$--.

Column 8, line 23, in the equation, replace "$n_r$" with --$\bar{n}_r$--.

Column 8, line 26, replace "$\alpha_{SC}$" with --$\bar{\alpha}_{sc}$--.

Column 8, line 26, replace "$\alpha_R$" with --$\bar{\alpha}_r$--.

Column 8, line 26, replace "$\alpha_M$" with --$\bar{\alpha}_m$--.

UNITED STATES PATENT AND TRADEMARK OFFICE
CERTIFICATE OF CORRECTION

PATENT NO. : 5,138,153
DATED : August 11, 1992
INVENTOR(S) : John S. Gergely et al.

It is certified that error appears in the above-indentified patent and that said Letters Patent is hereby corrected as shown below:

Column 8, line 35, in the equation, replace "$n_r$" with --$\bar{n}_r$--.

Column 8, line 38, in the equation, replace "$\alpha_{sc}$" (both occurrences) with --$\bar{\alpha}_{sc}$--.

Column 8, line 52, in the equation, replace "$n_r$" with --$\bar{n}_r$--.

Column 8, line 58, in the equation, replace "$n_r$" with --$\bar{n}_r$--.

Column 10, line 48, "got" should be --to--.

Column 10, line 58, after the word "cable" insert --means--.

Signed and Sealed this

Seventeenth Day of May, 1994

BRUCE LEHMAN

*Attest:*

*Attesting Officer*  *Commissioner of Patents and Trademarks*